United States Patent
Bianchi et al.

(10) Patent No.: US 9,776,984 B2
(45) Date of Patent: Oct. 3, 2017

(54) COMPOUNDS CONTAINING A PENTALENE UNIT AND PROCESS FOR THEIR PREPARATION

(71) Applicant: ENI S.P.A., Roma (IT)

(72) Inventors: Gabriele Bianchi, Novara (IT); Giuliana Schimperna, Novara (IT)

(73) Assignee: ENI S.p.A., Rome (IT)

( * ) Notice: Subject to any disclaimer, the term of this patent is extended or adjusted under 35 U.S.C. 154(b) by 144 days.

(21) Appl. No.: 14/890,824

(22) PCT Filed: Jul. 22, 2014

(86) PCT No.: PCT/IB2014/063308
§ 371 (c)(1),
(2) Date: Nov. 12, 2015

(87) PCT Pub. No.: WO2015/015368
PCT Pub. Date: Feb. 5, 2015

(65) Prior Publication Data
US 2016/0090371 A1 Mar. 31, 2016

(30) Foreign Application Priority Data
Jul. 31, 2013 (IT) .............................. MI2013A01295

(51) Int. Cl.
*C07D 333/16* (2006.01)
*C07D 333/18* (2006.01)
(Continued)

(52) U.S. Cl.
CPC ......... *C07D 333/16* (2013.01); *C07D 333/18* (2013.01); *C09K 11/06* (2013.01);
(Continued)

(58) Field of Classification Search
CPC .... C07D 333/18; C07D 333/16; C09K 11/06; H01L 51/00; H01L 51/0054; H01L 51/0068
See application file for complete search history.

(56) References Cited

U.S. PATENT DOCUMENTS

2009/0230854 A1* 9/2009 Kim ................. C07C 13/66 313/504
2012/0153271 A1 6/2012 Goto et al.

FOREIGN PATENT DOCUMENTS

CN 102596889 A 7/2012
WO WO 2014/021109 A1 * 2/2014

OTHER PUBLICATIONS

International Search Report issued Oct. 16, 2014 in PCT/IB2014/063308.
(Continued)

*Primary Examiner* — Caixia Lu
(74) *Attorney, Agent, or Firm* — Oblon, McClelland, Maier & Neustadt, L.L.P.

(57) ABSTRACT

Compound containing a pentalene unit having general formula (I) wherein $R_1$ and $R_2$, equal to or different from each other, are selected from: linear or branched $C_1$-$C_{20}$, preferably $C_2$-$C_{12}$, alkyl groups, saturated or unsaturated, optionally containing heteroatoms, cycloalkyl groups optionally substituted, linear or branched $C_1$-$C_{20}$, preferably $C_2$-$C_{12}$, alkoxyl groups, saturated or unsaturated, optionally substituted; or the groups $R_1$ and $R_2$ can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium; $R_3$ is selected from aryl groups optionally substituted, heteroaryl groups optionally substituted; n is 0 or 1; with the proviso that: when n is 0, X represents a covalent bond and Y represents a sulfur atom (S); when n is 1, X is equal to Y, and represents a CH group, or a nitrogen atom (N). Said compound containing a pentalene unit, as such or after suitable functionalization and polymerization, can be advantageously used in the construction of photovoltaic devices (or solar devices) such as, for example, photovoltaic cells (or solar cells), photovoltaic modules (or solar modules), on both rigid and flexible supports. Said compound containing a pentalene unit can also be advantageously used as a constitutive unit of luminescent solar concentrators (LSCs). Furthermore, said compound containing a pentalene unit can be advantageously used as precursor of monomeric units in the preparation of semiconductor polymers.

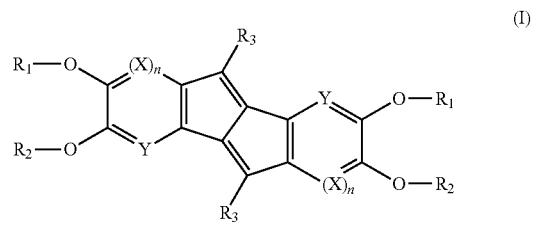

(I)

18 Claims, No Drawings

(51) Int. Cl.
*C09K 11/06* (2006.01)
*H01L 51/00* (2006.01)

(52) U.S. Cl.
CPC ...... *H01L 51/0036* (2013.01); *H01L 51/0054* (2013.01); *H01L 51/0068* (2013.01); *C09K 2211/1011* (2013.01); *C09K 2211/1092* (2013.01); *Y02E 10/549* (2013.01)

(56) References Cited

OTHER PUBLICATIONS

Takeshi Kawase et al., "Dinaphthopentalenes: Pentalene Derivatives for Organic Thin-Film Transistors", Angewandte Chemie (International Ed. Inenglish). vol. 122, No. 42, Oct. 11, 2010, XP055083792, pp. 7894-7898.

Takeshi Kawase et al.., "An Extremely Simple Dibenzopentalene Synthesis from 2-Bromo-1-ethynylbenzenes Using Nickel(0), Complexes: Construction of Its Derivatives with Various Functionalities ",Chemistry—A European Journal, vol. 15, No. 11, Mar. 2, 2009 , XP055083749, pp. 2653-2661.

Zerubba U. Levi, et al., "Versatile Synthesis of Pentalene Derivatives via the Pd-Catalyzed Homocoupling of Haloenynes", Journal of the American Chemical Society, vol. 131, No. 8, Mar. 4, 2009, XP055083845, pp. 2796-2797.

Jongtae Yang, et al., "Synthesis and Characterization of 5,10-Bis(2-thienyl)indeno[2,1- *a* ]indene Derivatives: The First Examples of Conducting Polymers Containing a Rigid Bis(thienyl)butadiene Core", The Journal of Organic Chemistry, vol. 1. 65, No. 20, Sep. 9, 2000 , XP055083843, pp. 6739-6742.

Tovar J. D, et al., "Functionalizable polycyclic aromatics through oxidative cyclization of pendant thiophenes", Journal of the American Chemical Society, ACS Publications, US, vol. 124, No. 26, Jun. 6, 2002 , XP002989180, pp. 7762-7769.

Jian Zhao, et al., "Pd-Catalyzed Cascade Crossover Annulation of *o*-Alkynylarylhalides and Diarylacetylenes Leading to Dibenzo[*a,e*]pentalenes ", Journal of the American Chemical Society, vol. 1. 135, No. 28, Jun. 28, 2013, XP055083948, pp. 10222-10225.

Hongyu Zhang, et al., "Intramolecular Reductive Double Cyclization of *o,o*-Bis(arylcarbonyl)diphenylacetylenes: Synthesis of Ladder π-Conjugated Skeletons", Organic Letters, vol. 11, No. 14, Jun. 18, 2009, XP055083963, pp. 3076-3079.

Jenna L. Jeffrey, et al., "An approach to the synthesis of dimeric resveratrol natural products via a palladium-catalyzed domino reaction", Tetrahedron Letters, Pergamon, vol. 50, No. 17, Feb. 14, 2009, XP025972752, pp. 1969-1972.

Takehisa Maekawa et al: "C-H activation route to dibenzo[a,e]pentalenes: annulation of arylacetylenes promoted by PdCl$_2$-AgOTf-*o*-chloranil", Chemical Science, vol. 4, No. 6, Mar. 20, 2013, XP055083958, p. 2369.

Masaichi Saito: "Synthesis and Reactions of Dibenzo[*a,e*]pentalenes", Symmetry, vol. 2, No. 2, Apr. 21, 2010, XP055083989, pp. 950-969.

Chao Hu, et al., "Dithieno [ *a,e*]pentalene Based Conjugated Polymers: Synthesis and Characterization", Chinese Journal of Chemistry, vol. 31, No. 11, XP055083947, Oct. 2, 2013, pp. 1404-1408.

Combined Chinese Office Action and Search Report issued Jul. 19, 2016 in Patent Application No. 201480034018.1 (with English language translation).

* cited by examiner

COMPOUNDS CONTAINING A PENTALENE UNIT AND PROCESS FOR THEIR PREPARATION

The present invention relates to a compound containing a pentalene unit.

More specifically, the present invention relates to a compound containing a pentalene unit substituted with alkoxyl groups.

The present invention also relates to a process for the preparation of said compound containing a pentalene unit through a reductive homocoupling reaction of a halogenated alkoxy-aromatic or alkoxy-heteroaromatic compound substituted in ortho position with an aryl-alkyne or heteroaryl-alkyne group in the presence of a catalyst containing palladium.

Said compound containing a pentalene unit, as such or after suitable functionalization and polymerization, can be advantageously used in the construction of photovoltaic devices (or solar devices) such as, for example, photovoltaic cells (or solar cells), photovoltaic modules (or solar modules), on both rigid and flexible supports. Said compound containing a pentalene unit can also be advantageously used as a constitutive unit of luminescent solar concentrators (LSCs). Furthermore, said compound containing a pentalene unit can be advantageously used as precursor of monomeric units in the preparation of semiconductor polymers.

Photovoltaic devices (or solar devices) are capable of converting the energy of a light radiation into electric energy. At present, most photovoltaic devices (or solar devices) which can be used for practical applications, exploit the physico-chemical properties of photoactive materials of the inorganic type, in particular high-purity crystalline silicon. As a result of the high production costs of silicon, however, scientific research has been orienting its efforts towards the development of alternative materials of the organic type having a conjugated, oligomeric or polymeric structure, in order to obtain organic photovoltaic devices (or solar devices) such as, for example, organic photovoltaic cells (or solar cells). Unlike high-purity crystalline silicon, in fact, said materials of the organic type are characterized by a relative synthesis facility, a low production cost, a reduced weight of the relative organic photovoltaic devices (or solar devices), and also allow the recycling of said materials of the organic type at the end of the life cycle of the organic photovoltaic device (or solar device) in which they are used.

The advantages indicated above make the use of said materials of the organic type energetically and economically interesting in spite of possible lower efficiencies (η) of the organic photovoltaic devices (or solar devices) thus obtained with respect to inorganic photovoltaic devices (or solar devices).

The functioning of the organic photovoltaic devices (or solar devices) such as, for example, organic photovoltaic cells (or solar cells), is based on the combined use of an electron-acceptor compound and an electron-donor compound. In the state of the art, the most widely used electron-acceptor compounds in organic photovoltaic devices (or solar devices) are fullerene derivatives, in particular PC61BM (6,6-phenyl-$C_{61}$-butyric acid methyl ester) or PC71BM (6,6-phenyl-$C_{71}$-butyric acid methyl ester), which have reached the higher efficiencies when mixed with electron-donor compounds selected from π-conjugated polymers such as, for example, polythiophenes (η>5%), polycarbazoles (η>6%), derivatives of poly-(thienothiophene)-benzodithiophene (PTB) (η>8%).

The basic conversion process of light into electric current in an organic photovoltaic cell (or solar cell) takes place through the following steps:
1. absorption of a photon on the part of the electron-donor compound with the formation of an exciton, i.e. a pair of "electron-electronic gap (or hole)" charge transporters;
2. diffusion of the exciton in a region of the electron-donor compound as far as the interface with the electron-acceptor compound;
3. dissociation of the exciton in the two charge transporters: electron (−) in the acceptor phase (i.e. in the electron-acceptor compound) and electronic gap [or hole) (+)] in the donor phase (i.e. in the electron-donor compound);
4. transporting of the charges thus formed to the cathode (electron, through the electron-acceptor compound) and to the anode [electronic gap (or hole) through the electron-donor compound], with the generation of an electric current in the circuit of the organic photovoltaic cell (or solar cell).

The photo-absorption process with the formation of the exciton and subsequent yielding of the electron to the electron-acceptor compound leads to the excitation of an electron from the HOMO (Highest Occupied Molecular Orbital) to the LUMO (Lowest Unoccupied Molecular Orbital) of the electron-donor compound, and subsequently the passage from this to the LUMO of the electron-acceptor compound.

As the efficiency of an organic photovoltaic cell (or solar cell) depends on the number of free electrons that are generated by dissociation of the excitons which, in their turn, can be directly correlated with the number of photons absorbed, one of the structural characteristics of the electron-donor compounds which mostly influences said efficiency is the difference in energy existing between the HOMO and LUMO orbitals of the electron-donor compound, i.e. the so-called band-gap. The maximum wavelength value at which the electron-donor compound is capable of collecting and of effectively converting photons into electric energy, i.e. the so-called "light-harvesting" or "photon harvesting" process, depends, in particular, on said difference. In order to obtain acceptable electric currents, the band-gap, i.e. the difference in energy between HOMO and LUMO of the donor compound, must not be excessively high to allow the absorption of the highest number of photons, but at the same time not excessively low as it could reduce the voltage at the electrodes of the device.

In the simplest way of operating, the organic photovoltaic cells (or solar cells) are produced by introducing a thin layer (about 100 nanometers) of a mixture of the electron-acceptor compound and of the electron-donor compound (architecture known as "bulk heterojunction"), between two electrodes, normally consisting of indium-tin oxide (ITO) (anode) and aluminium (Al) (cathode). In order to produce a layer of this type, a solution of the two compounds is generally prepared and a photoactive film is subsequently created on the anode [indium-tin oxide (ITO] starting from this solution, resorting to suitable deposition techniques such as, for example, "spin-coating", "spray-coating" "ink-jet printing", and the like. Finally, the counter-electrode [i.e. the aluminium cathode (Al)] is deposited on the dried film. Optionally, other additional layers capable of exerting specific functions of an electric, optical, or mechanical nature, can be introduced between the electrodes and the photoactive film.

Generally, in order to facilitate the electron gaps (or holes) in reaching the anode [indium-tin oxide (ITO)] and at the same time in blocking the transporting of electrons, thus improving the collection of the charges on the part of the electrode and inhibiting recombination phenomena, before creating the photoactive film starting from the mixture of the acceptor compound and of the donor compound as described above, a film is deposited, starting from an aqueous suspension of PEDOT:PSS [poly(3,4-ethylenedioxythiophene) polystyrene sulfonate], resorting to suitable deposition techniques such as, for example, "spin-coating", "spray-coating" "ink-jet printing", and the like.

The electron-donor compound which is most commonly used in the construction of organic photovoltaic cells (or solar cells) is regioregular poly(3-hexylthiophene) (P3HT). This polymer has optimal electronic and optical characteristics (good HOMO and LUMO orbital values, good molar adsorption coefficient), a good solubility in the solvents used in the construction of photovoltaic cells (or solar cells) and a reasonable mobility of the electronic gaps.

Other examples of polymers which can be advantageously used as electron-donor compounds are: the polymer PCDTBT {poly[N-9''-heptadecanyl-2,7-carbazole-alt-5,5-(4',7'-di-2-thienyl-2',1',3'-benzothiadiazole]}, the polymer PCPDTBT {poly[2,6-(4,4-bis-(2-ethylhexyl)-4H-cyclopenta[2,1-b;3,4-b']-dithio-phene)-alt-4,7-(2,1,3-benzothiadiazole)]}.

Electron-donor compounds containing benzodithiophene units having a structure similar to poly(3-hexylthiophene) (P3HT) are also known, wherein the thiophene units, however, are planarized by means of benzene rings. This characteristic not only increases the oxidation potential of said electron-donor compounds but also improves their stability to air and increases the molecular order during the formation of the photoactive film: this leads to excellent charge transporting properties [electrons or electronic gaps (holes)]. The use of electron-donor compounds containing benzodithiophene units therefore enables the production of photovoltaic devices (or solar devices) having improved performances with respect to the use of poly(3-hexylthiophene) (P3HT).

It is also known that compounds containing a pentalene unit not only have the characteristics of the above electron-donor compounds containing benzodithiophene units, but also have a diradical character typical of condensed aromatic rings with $4n\pi$ electrons: said characteristic involves a considerable increase in the life time of the exciton during the diffusion of the same in a region of the electron-donor compound up to the interface with the electron-acceptor compound. Further details relating to said characteristic can be found, for example, in the article of Nakano M. et al.: "Diradical Character Based Design for Singlet Fission of Condensed-Ring Systems with $4n\pi$ Electrons", *"The Journal of Physical Chemistry C"* (2012), Vol. 116, pages 19729-19736.

Consequently, the use of electron-donor compounds containing a pentalene unit can allow photovoltaic devices (or solar devices) to be produced with further improved performances.

Processes for the preparation of compounds containing a pentalene unit are known in the art, in particular for the preparation of compounds containing a dibenzopentalene unit.

The dibenzopentalene can be obtained, for example, by the flash vacuum pyrolysis of 1,4-diphenylbutadiyne as described, for example, by Brown R. F. C. et al. in the article: "The ethyne-ethylidene rearrangement: Formation of Indeno[2,1-a]indene and fluoranthene on flash vacuum pyrolisis of 1,4-diphenylbutadiyne", *"Tetrahedron Letters"* (2013), Vol. 34, Issue 22, pages 3607-3608.

Or, the dibenzopentalene can be obtained by reaction of benzaldehyde with benzyl cyanide to give 2,3-diphenyl succinonitrile which is subsequently subjected to hydrolysis to give 2,3-diphenylsuccinic acid. Said 2,3-diphenylsuccinic acid is cyclized with sulfuric acid to give a diketone which is subsequently subjected to the action of a Grignard reagent (i.e. 2-bromomagnesiumthiophene) as described, for example, by Cava M. P. et al. in the article: "Synthesis and characterization of 5,10-Bis(2-thienyl)indeno[2,1-a]indene Derivatives: The First Examples of Conducting Polymers Containing a Rigid Bis(thienyl)butadiene Core", *"The Journal of Organic Chemistry"* (2000), Vol. 65, pages 6739-6742.

Or, pentalene derivatives can be synthesized by the reductive homocoupling reaction of haloenynes, as described, for example by Tilley T. D. et al. in the article: "Versatile Synthesis of Pentalene Derivatives via the Pd-catalyzed Homocoupling of Haloenynes", *"The Journal of American Chemical Society"* (2009), Vol. 131, pages 2796-2797.

As indicated above, as the use of electron-donor compounds containing a pentalene unit can allow photovoltaic devices (or solar devices) to be produced with further improved performances, the study of new electron-donor compounds containing a pentalene unit is still of great interest.

The Applicant has therefore considered the problem of finding a compound containing a pentalene unit which can be used, as such or after suitable functionalization and polymerization, as an electron-donor compound.

The Applicant has now found a compound containing a pentalene unit substituted with alkoxyl groups which, as such or after suitable functionalization and polymerization, can be advantageously used in the construction of photovoltaic devices (or solar devices) such as, for example, photovoltaic cells (or solar cells), photovoltaic modules (or solar modules), on both rigid and flexible supports. Said compound containing a pentalene unit can also be advantageously used as a constitutive unit of luminescent solar concentrators (LSCs). Furthermore, said compound containing a pentalene unit can be advantageously used as precursor of monomeric units in the preparation of semiconductor polymers.

An object of the present invention therefore relates to a compound containing a pentalene unit having general formula (I):

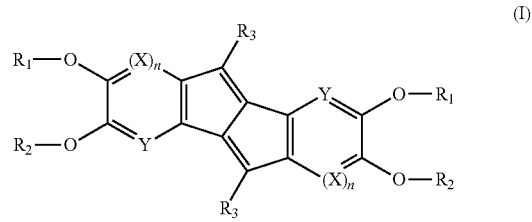

wherein:
R$_1$ and R$_2$, equal to or different from each other, are selected from: linear or branched C$_1$-C$_{20}$, preferably C$_2$-C$_{12}$, alkyl groups, saturated or unsaturated, optionally containing heteroatoms, cycloalkyl groups optionally substituted, linear or branched C$_1$-C$_{20}$, preferably C$_2$-C$_{12}$, alkoxyl groups, saturated or unsaturated, optionally substituted;
or R$_1$ and R$_2$ can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;

$R_3$ is selected from aryl groups optionally substituted, heteroaryl groups optionally substituted;

n is 0 or 1;

with the proviso that:

when n is 0, X represents a covalent bond and Y represents a sulfur atom (S);

when n is 1, X is equal to Y, and represents a CH group, or a nitrogen atom (N).

According to a preferred embodiment of the present invention, in said general formula (I):

$R_1$ and $R_2$, the same as each other, are selected from branched $C_2$-$C_{12}$ alkyl groups, and are preferably a 2-ethylhexyloxyl group;

$R_3$ is selected from heteroaryl groups optionally substituted, and is preferably a thienyl group;

n is 1;

X is equal to Y, and represents a CH group.

The present invention also relates to a process for the preparation of a compound containing a pentalene unit having general formula (I).

A further object of the present invention therefore relates to a process for the preparation of a compound containing a pentalene unit having general formula (I):

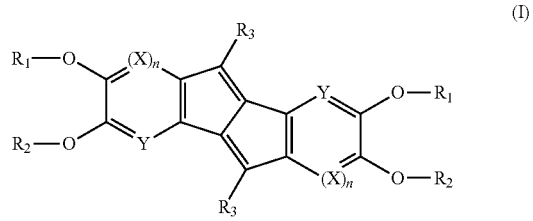

(I)

wherein $R_1$, $R_2$, $R_3$, X, Y and n, have the same meanings described above, through a reductive homocoupling reaction of a halogenated alkoxy-aromatic or alkoxy-heteroaromatic compound having general formula (II):

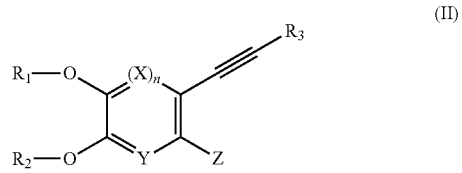

(II)

wherein $R_1$, $R_2$, $R_3$, X, Y and n, have the same meanings described above, Z represents a halogen atom selected from bromine, chlorine, iodine, preferably bromine, in the presence of at least one catalyst containing palladium.

For the aim of the present description and of the following claims, the definitions of the numerical ranges always comprise the extremes unless otherwise specified.

For the aim of the present description and of the following claims, the term "comprising" also includes the terms "which essentially consists of" or "which consists of".

The term "$C_1$-$C_{20}$ alkyl groups" means linear or branched alkyl groups having from 1 to 20 carbon atoms, saturated or unsaturated. Specific examples of $C_1$-$C_{20}$ alkyl groups are: methyl, ethyl, n-propyl, iso-propyl, n-butyl, iso-butyl, t-butyl, pentyl, ethyl-hexyl, hexyl, heptyl, octyl, nonyl, decyl, dodecyl.

The term "$C_1$-$C_{20}$ alkyl groups optionally containing heteroatoms" means linear or branched alkyl groups having from 1 to 20 carbon atoms, saturated or unsaturated, wherein at least one of the hydrogen atoms is substituted with a heteroatom selected from: halogens such as, for example, fluorine, chlorine, preferably fluorine; nitrogen; sulfur; oxygen. Specific examples of $C_1$-$C_{20}$ alkyl groups optionally containing heteroatoms are: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl, perfluoropentyl, perfluorooctyl, perfluorodecyl, oxymethyl, thiomethyl, thioethyl, dimethylamine, propylamine, dioctylamine.

The term "cycloalkyl groups" means cycloalkyl groups having from 3 to 30 carbon atoms. Said cycloalkyl groups can be optionally substituted with one or more groups, equal to or different from each other, selected from: halogen atoms such as, for example, fluorine, chlorine, bromine, preferably fluorine; hydroxyl groups; $C_1$-$C_{12}$ alkyl groups; $C_1$-$C_{12}$ alkoxyl groups; $C_1$-$C_{12}$ thioalkoxyl groups; $C_3$-$C_{24}$ tri-alkylsilyl groups; polyethyleneoxyl groups; cyano groups; amino groups; $C_1$-$C_{12}$ mono- or di-alkylamine groups; nitro groups. Specific examples of cycloalkyl groups are: cyclopropyl, 2,2-difluorocyclopropyl, ciclobutyl, ciclopentyl, ciclohexyl, methylcyclohexyl, methoxycyclohexyl, fluorocyclohexyl, phenylcyclohexyl, decalin, abiethyl.

The term "$C_1$-$C_{20}$ alkoxyl groups" means groups comprising an oxygen atom to which a linear or branched, saturated or unsaturated, $C_1$-$C_{20}$ alkyl group is bound. Specific examples of $C_1$-$C_{20}$ alkoxyl groups are: methoxyl, ethoxyl, n-propoxyl, iso-propoxyl, n-butoxyl, iso-butoxyl, t-butoxyl, pentoxyl, hexyloxyl, 2-ethylhexyloxyl, heptyloxyl, octyloxyl, nonyloxyl, decyloxyl, dodecyloxyl.

The term "cyclo or polycyclic system" means a system containing one or more rings containing from 3 to 14 carbon atoms, optionally containing heteroatoms selected from nitrogen, oxygen, sulfur, silicon, selenium, phosphorus. Specific examples of cyclo or polycyclic system are: thiadiazole, benzothiophene, quinoxazoline, pyridine.

The term "aryl groups" means aromatic carbocyclic groups containing from 6 to 60 carbon atoms. Said aryl groups can be optionally substituted with one or more groups, equal to or different from each other, selected from: halogen atoms such as, for example, fluorine, chlorine, bromine, preferably fluorine; hydroxyl groups; $C_1$-$C_{12}$ alkyl groups; $C_1$-$C_{12}$ alkoxyl groups; $C_1$-$C_{12}$ thioalkoxyl groups; $C_3$-$C_{24}$ tri-alkylsilyl groups; polyethyleneoxyl groups; cyano groups; amino groups; $C_1$-$C_{12}$ mono- or di-alkylamine groups; nitro groups. Specific examples of aryl groups are: phenyl, methylphenyl, trimethylphenyl, methoxyphenyl, hydroxyphenyl, phenyloxyphenyl, fluorophenyl, pentafluorophenyl, chlorophenyl, bromophenyl, nitrophenyl, dime thylaminophenyl, naphthyl, phenylnaphthyl, phenanthrene, anthracene.

The term "heteroaryl groups" means aromatic heterocyclic groups, penta- or hexa-atomic, also benzocondensed or heterobicyclic, containing from 4 to carbon atoms and from 1 to 4 heteroatoms selected from nitrogen, oxygen, sulfur, silicon, selenium, phosphorus. Said heteroaryl groups can be optionally substituted with one or more groups, equal to or different from each other, selected from: halogen atoms such as, for example, fluorine, bromine, chlorine, preferably fluorine; hydroxyl groups; $C_1$-$C_{12}$ alkyl groups; $C_1$-$C_{12}$ alkoxyl groups; $C_1$-$C_{12}$ thioalkoxyl groups; $C_3$-$C_{24}$ tri-alkylsilyl groups; polyethyleneoxyl groups; cyano groups; amino groups; $C_1$-$C_{12}$ mono- or di-alkylamine groups; nitro groups. Specific examples of heteroaryl groups are: pyridine, methylpyridine, methoxypyridine, phenylpyridine, fluoropyridine, pyrimidine, pyridazine, pyrazine, triazine, tetrazine, quinoline, quinoxaline, quinazoline, furan, thiophene, hexylthiophene, bromothiophene, dibromothiophene, pyrrole, oxazole, triazole, isooxazole, isothiazole, oxadiazole, thiadiazole, pyrazole, imidazole, triazole, tetrazole, indole, benzofuran, benzothiophene, benzooxazole, benzothiazole, benzooxadiazole, benzothiadiazole, benzopyrazole, benzimidazole, benzotriazole, triazolepyridine, triazolepyrimidine, coumarin.

The process, object of the present invention, can be carried out according to the following Scheme 1:

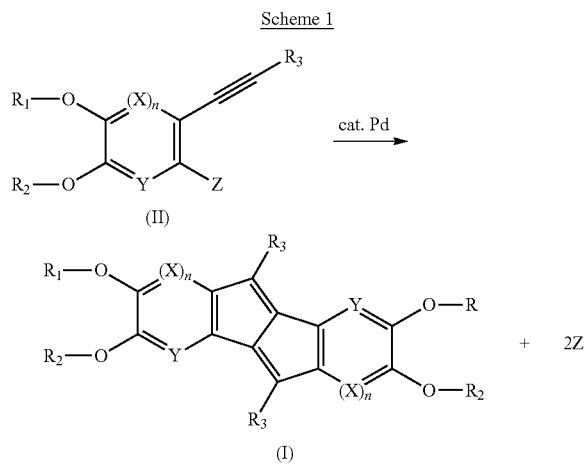

wherein $R_1$, $R_2$, $R_3$, X, Y, n and Z, have the same meanings described above and "cat. Pd" is the catalyst containing palladium.

According to a preferred embodiment of the present invention, said catalyst containing palladium can be selected, for example, from: compounds of palladium in oxidation state 0 or +2 such as, for example, palladium(II) chloride [$PdCl_2$], palladium(II)acetate [$Pd(OAc)_2$], tris (dibenzylidene)palladium(0) [$Pd_2(dba)_3$ wherein $dba=C_6H_5CH=CHCOCH=CHC_6H_5$], bis(acetonitrile)-palladium(II)chloride [$Pd(CH_3CN)_2CH_2$], bis(triphenylphosphine)palladium(II)chloride [$Pd(PPh_3)_2CH_2$], bis-(triphenylphosphine)palladium(II) acetate [$Pd(PPh_3)_2(OAc)_2$], tetrakis(triphenylphosphine)-palladium(0) [$Pd(PPh_3)_4$], or mixtures thereof. Said catalyst containing palladium is preferably tris(dibenzylidene)palladium(0) [$Pd_2(dba)_3$ wherein $dba=C_6H_5CH=CHCOCH=CHC_6H_5$].

According to a preferred embodiment of the present invention, said halogenated alkoxy-aromatic or alkoxy-heteroaromatic compound having general formula (II) and said catalyst containing palladium can be used in a molar ratio ranging from 100:0.1 to 100:6, preferably ranging from 100:0.2 to 100:4.

According to a preferred embodiment of the present invention, said process can be carried out in the presence of at least one weak organic base.

According to a preferred embodiment of the present invention, said weak organic base can be selected, for example, from: carboxylates of alkaline metals (e.g., sodium, potassium, caesium) or of alkaline-earth metals (e.g., magnesium, calcium) such as, for example, potassium acetate, sodium acetate, caesium acetate, magnesium acetate, calcium acetate, potassium propionate, sodium propionate, caesium propionate, magnesium propionate, calcium propionate, or mixtures thereof; carbonates of alkaline metals (e.g., lithium, sodium, potassium, caesium) or of alkaline-earth metals (e.g., magnesium, calcium) such as, for example, lithium carbonate, potassium carbonate, sodium carbonate, caesium carbonate, magnesium carbonate, calcium carbonate, or mixtures thereof; bicarbonates of alkaline metals (e.g., lithium, sodium, potassium, caesium) or of alkaline-earth metals (e.g., magnesium, calcium) such as, for example, lithium bicarbonate, potassium bicarbonate, sodium bicarbonate, caesium bicarbonate, magnesium bicarbonate, calcium bicarbonate, or mixtures thereof; or mixtures thereof. Said weak organic base is preferably selected from caesium carbonate, potassium carbonate.

According to a preferred embodiment of the present invention, said halogenated alkoxy-aromatic or alkoxy-heteroaromatic compound having general formula (II) and said weak organic base can be used in a molar ratio ranging from 1:2.2 to 1:20, preferably ranging from 1:2.5 to 1:4.

According to a preferred embodiment of the present invention, said process can be carried out in the presence of at least one organic reducing agent.

According to a preferred embodiment of the present invention, said organic reducing agent can be selected, for example, from: hydroquinone, pyrocatechol, para-hydroxyaminobenzene. Said organic reducing agent is preferably hydroquinone.

According to a preferred embodiment of the present invention, said halogenated alkoxy-aromatic or alkoxy-heteroaromatic compound having general formula (II) and said organic reducing agent can be used in molar ratios ranging from 1:1.5 to 1:10, preferably ranging from 1:2 to 1:4.

According to a preferred embodiment of the present invention, said halogenated alkoxy-aromatic or alkoxy-heteroaromatic compound having general formula (II) can be used at a molar concentration ranging from 0.1 mmoles to 10 mmoles, preferably ranging from 0.5 mmoles to 1.0 mmoles.

According to a preferred embodiment of the present invention, said process can be carried out in the presence of at least one polar aprotic organic solvent.

According to a preferred embodiment of the present invention, said polar aprotic organic solvent can be selected, for example, from: diethyl ether ($Et_2O$), tetrahydrofuran (THF), 1,4-dioxane, dimethylsulfoxide (DMSO), N-methylpyrrolidone (NMP), N,N-dimethylformamide (DMF), or mixtures thereof. Said polar aprotic organic solvent is preferably selected from tetrahydrofuran (THF), 1,4-dioxane.

According to a preferred embodiment of the present invention, said halogenated alkoxy-aromatic or alkoxy-heteroaromatic compound having general formula (II) can be used in said polar aprotic organic solvent in such a quantity so as to have a molar concentration in said solvent ranging from 0.05 mmoles to 2.0 mmoles, preferably ranging from 0.1 mmoles to 1.5 mmoles.

According to a preferred embodiment of the present invention, said process can be carried out in the presence of at least one ligand of the catalyst containing palladium.

According to a preferred embodiment of the present invention, said ligand can be selected, for example, from: tri(t-butyl)phosphine, triphenylphosphine, tricyclohexylphosphonium tetrafluoroborate, 2-dicyclohexylphosphine-2'-(N,N-dimethyl-amino)biphenyl (DavePhos), di-t-butyl (methyl)phosphonium tetrafluoroborate, tri-t-butyl(methyl)

phosphonium tetrafluoroborate, or mixtures thereof. Said ligand is preferably tri(t-butyl)phosphine.

According to a preferred embodiment of the present invention, said halogenated alkoxy-aromatic or alkoxy-heteroaromatic compound having general formula (II) and said ligand can be used in molar ratios ranging from 100:1 to 100:10, preferably ranging from 100:3 to 100:6.

According to a preferred embodiment of the present invention, said process can be carried out at a temperature ranging from 80° C. to 170°, preferably ranging from 100° C. to 150°.

According to a preferred embodiment of the present invention, said process can be carried out for a time ranging from 12 hours to 72 hours, preferably ranging from 16 hours to 48 hours.

The halogenated alkoxy-aromatic or alkoxy-heteroaromatic compound having general formula (II) can be obtained according to processes known in the art, for example by means of Sonogashira coupling between a halogenated aromatic compound and a terminal alkyne. Further details relating to said processes can be found, for example, in the article of Buchwald, S. L. et al.: "Domino Cu-Catalyzed C—N Coupling/Hydroamidation: A highly Efficient Synthesis of Nitrogen Heterocycles", "Angewandte Chemie International Edition" (2006), Vol. 45, No. 42, pages 7079-7082; or in the article of Takahashi, T. et al.: "Alkynylzirconation of Alkynes and Application to One-Pot Bisalkynylation of Alkynes", "The Journal of Organic Chemistry" (2002), Vol. 67, No. 21, pages 7451-7456.

The present invention also relates to the use of said compound containing a pentalene unit having general formula (I), as such or after suitable functionalization and polymerization, in the construction of photovoltaic devices (or solar devices) such as photovoltaic cells (or solar cells), photovoltaic modules (or solar modules), on both rigid and flexible supports.

The present invention also relates to the use of said compound containing a pentalene unit having general formula (I) as a constitutive unit of luminescent solar concentrators (LSCs).

The present invention also relates to the use of said compound containing a pentalene unit having general formula (I) as a precursor of monomeric units in the preparation of semiconductor polymers.

Some illustrative and non-limiting examples are provided hereunder for a better understanding of the present invention and for its practical embodiment.

EXAMPLE 1

Preparation of 4,5-bis(2-ethylhexyloxy)-2-bromoiodobenzene (a) Preparation of 1,2-bis(2-ethylhexyloxy)benzene having Formula (a)

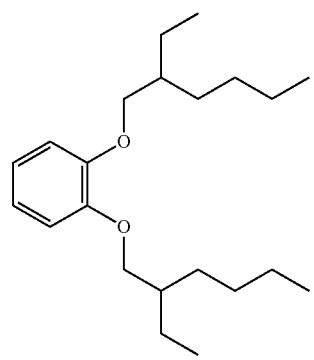

(a)

2-ethylhexylbromide (Aldrich) (11.39 g; 59.0 mmoles) and potassium carbonate (Aldrich) (9.5 g; 69.0 mmoles) were added, in a two-necked Pyrex glass flask, under an inert atmosphere, to a solution of catechol (Aldrich) (2.5 g; 22.7 mmoles) in anhydrous N,N-dimethylformamide (Aldrich) (20 ml), and the temperature was brought to 95° C. After 18 hours, the reaction mixture obtained was poured into water and extracted with ethyl ether (Carlo Erba) (3×25 ml). The organic phase obtained was washed to neutrality with water (3×25 ml), and subsequently anhydrified on sodium sulfate (Aldrich): the residual solvent was removed by distillation at reduced pressure. The residue obtained was purified by elution on a silica gel chromatographic column [(eluent: n-heptane) (Carlo Erba)], obtaining 7.2 g of 1,2-bis(2-ethylhexyloxy)benzene (yield 95%).

(b) Preparation of 1,2-bis(2-ethylhexyloxy)-4-bromobenzene having Formula (b)

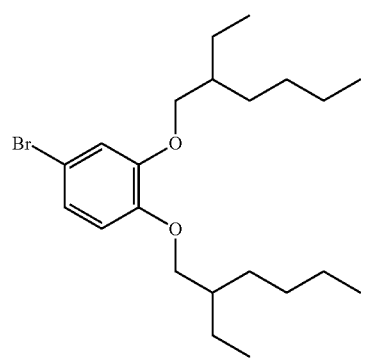

(b)

EXAMPLE 1

N-bromosuccinimide (NBS) (Aldrich) (3.9 g; 22.0 mmoles) was added, in a two-necked Pyrex glass flask, under an inert atmosphere, to a solution of 1,2-bis(2-ethylhexyloxy)benzene (7.4 g; 22.0 mmoles), obtained as described in (a), in 39 ml of anhydrous tetrahydrofuran (THF) (Aldrich): the solution obtained was left in the dark, under stirring. After 18 hours, the reaction mixture obtained was poured into water and extracted with ethyl ether (Carlo Erba) (3×25 ml). The organic phase obtained was washed to neutrality with water (3×25 ml), and subsequently anhydrified on sodium sulfate (Aldrich): the residual solvent was removed by distillation at reduced pressure. The residue obtained was purified by elution on a silica gel chromatographic column [(eluent: n-heptane) (Carlo Erba)], obtaining 7.5 g of 1,2-bis(2-ethylhexyloxy)-4-bromobenzene (yield 83%).

(c) Preparation of 1,2-bis(2-ethylhexyloxy)-4-bromo-5-iodobenzene having Formula (c)

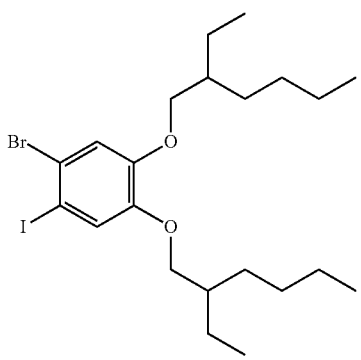

(c)

N-iodosuccinimide (NIS) (Aldrich) (4.7 g; 20.9 mmoles) was added, in a two-necked Pyrex glass flask, under an inert atmosphere, to a solution of 1,2-bis(2-ethylhexyloxy)-4-bromobenzene (7.5 g; 18.2 mmoles), obtained as described in (b), in 18 ml of chloroform (Carlo Erba) and 18 ml of acetic acid (Carlo Erba): the solution obtained was left in the dark, under stirring. After 12 hours, the reaction mixture obtained was poured into water and extracted with dichloromethane (Carlo Erba) (3×25 ml). The organic phase obtained was washed first with an aqueous solution of sodium thiosulfate 0.1 N (Aldrich) (3×25 ml), then with water (3×25 ml), subsequently with a saturated aqueous solution of sodium bicarbonate [NaHCO$_{3(sat.)}$] (prepared with sodium bicarbonate of Aldrich) [NaHCO$_{3(sat.)}$] (3×25 ml), and finally to neutrality with water, and subsequently anhydrified on sodium sulfate (Aldrich): the residual solvent was removed by distillation at reduced pressure. The residue obtained was purified by elution on a silica gel chromatographic column [(eluent: n-heptane) (Carlo Erba)], obtaining 6.7 g of 1,2-bis(2-ethylhexyloxy)-4-bromo-5-iodobenzene (yield 68%).

ESEMPIO 2

Preparation of 4,5-bis(2-ethylhexyloxy)-1-bromo-2-(2-(2-thienyl)ethinyl)benzene having Formula (IIa)

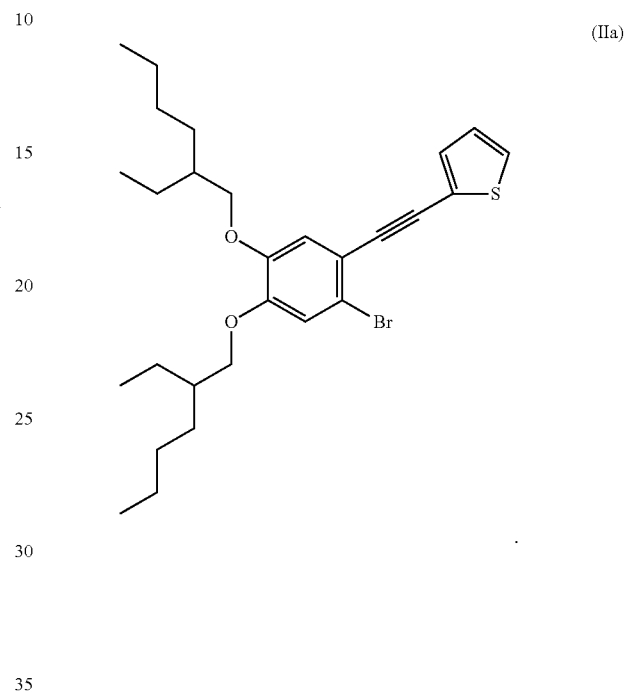

(IIa)

The following products were charged, in order, under an inert atmosphere, into a tailed Pyrex glass test-tube equipped with a screw stopper: 540 mg of 4,5-bis(2-ethylhexyloxy)-2-bromoiodobenzene (1.0 mmoles) obtained as described in Example 1, 150 mg of 2-[trimethylsilyl(ethinyl)]thiophene (0.83 mmoles) (Aldrich) dissolved in 5 ml of N,N-dimethylformamide (Aldrich), 35 mg of bis(triphenylphosphine)-palladium(II)chloride [Pd(PPh$_3$)$_2$CH$_2$] (Aldrich) (0.05 mmoles), 2 mg of copper(I)iodide (CuI) (Aldrich) (0.01 mmoles), 304 mg of triethylamine (Aldrich) (3.0 mmoles) and finally 379 mg of tetra-n-butylammonium fluoride (Aldrich) (1.0 mmoles). After closing the reactor, this was placed in an oil bath preheated to 50° C., for 4 hours. After cooling to room temperature (25° C.), an aqueous solution of hydrochloric acid 0.1 M (Aldrich) (50 ml) was added to the reaction mixture and the whole mixture was extracted with diethyl ether (Carlo Erba) (3×25 ml). The organic phase obtained was washed to neutrality with water (3×25 ml), and subsequently anhydrified on sodium sulfate (Aldrich) and evaporated. The residue obtained was purified by elution on a silica gel chromatographic column [(eluent: heptane) (Carlo Erba)], obtaining 425 mg of 4,5-bis(2-ethylhexyloxy)-1-bromo-2-(2-(2-thienyl)ethinyl)benzene as a yellow oil (yield 99%).

ESEMPIO 3

Preparation of 5,10-dithienyl-2,3,7,8-tetra(2-ethyl-hexyloxy)indeno[2,1-a]indene having Formula (Ia)

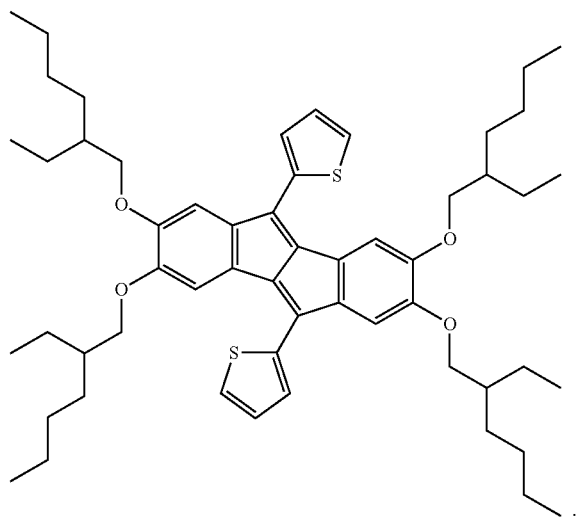

(Ia)

The following products were charged, in order, under an inert atmosphere, into a tailed Pyrex glass test-tube equipped with a screw stopper: 326 mg of caesium carbonate ($Cs_2CO_3$) (Aldrich) (1.0 mmoles), 111 mg of hydroquinone (Aldrich) (1.0 mmoles), 167 mg of caesium fluoride (CsF) (Aldrich) (1.1 mmoles), 6.07 mg of tri(t-butyl)phosphine [$P(tBu)_3$] (Aldrich) (0.03 mmoles), 6.87 mg of tris(dibenzylidene-acetone)palladium(0) [$Pd_2(dba)_3$ wherein dba=$C_6H_5CH$=$CHCOCH$=$CHC_6H_5$] (Aldrich) (0.0075 mmoles) and finally 260 mg of 4,5-bis(2-ethylhexyloxy)-1-bromo-2-(2-(2-thienyl)ethinyl)benzene (IIa), obtained as described in Example 2, dissolved in 5 ml of 1,4-dioxane (Aldrich). After closing the reactor, this was placed in an oil bath preheated to 130° C., for 24 hours. After cooling to room temperature (25° C.), a saturated solution of sodium chloride [$NaCl_{(sat.)}$] (prepared with sodium chloride of Aldrich) [NaCl], was added to the reaction mixture and the whole mixture was extracted with diethyl ether (Carlo Erba) (3×25 ml). The organic phase was subsequently anhydrified on sodium sulfate (Aldrich) and evaporated. The residue obtained was purified by elution on a silica gel chromatographic column [(eluent: heptane) (Carlo Erba)], obtaining 242 mg of 5,10-dithienyl-2,3,7,8-tetra(2-ethylhexyloxy)indeno-[2,1-a]indene as a red solid (yield 55%).

The invention claimed is:

1. A compound comprising containing a pentalene unit having a general formula (I):

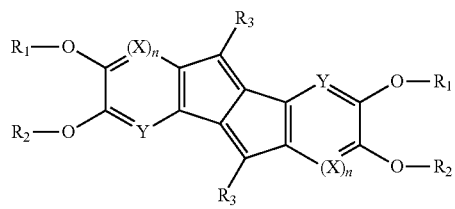

(I)

wherein:
R₁ and R₂, equal to or different from each other, are linear or branched $C_1$-$C_{20}$ alkyl groups, saturated or unsaturated, optionally containing heteroatoms, optionally substituted cycloalkyl groups, optionally substituted linear or branched $C_1$-$C_{20}$ alkoxyl groups, saturated or unsaturated; or
R₁ and R₂ are optionally bound to each other so as to form, together with carbon atoms to which they are bound, a cycle or a polycyclic system comprising from 3 to 14 carbon atoms, wherein the cycle or the polycyclic system is saturated, unsaturated, or aromatic, and the cycle or the polycyclic system optionally comprises a heteroatom;
R₃ is an optionally substituted aryl group or an optionally substituted heteroaryl group;
n is 0 or 1;
with the proviso that:
when n is 0, X represents a covalent bond and Y represents a sulfur atom (S);
when n is 1, X is equal to Y, and represents a CH group or a nitrogen atom (N).

2. The compound according to claim 1, wherein:
R₁ and R₂ are branched $C_2$-$C_{12}$ alkyl groups, and R₁ is equal to R₂;
R₃ is an optionally substituted heteroaryl group;
n is 1; and
X is equal to Y, and represents a CH group.

3. A process for preparing the compound according to claim 1, comprising:
performing a reductive homocoupling reaction of a halogenated alkoxy-aromatic or alkoxy-heteroaromatic compound having a general formula (II):

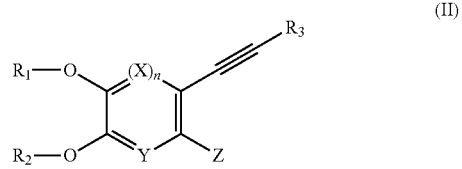

(II)

wherein Z represents a halogen atom selected from the group consisting of bromine, chlorine, and iodine, wherein the reductive homocoupling reaction is performed in the presence of a catalyst comprising palladium in oxidation state 0 or +2.

4. The process according to claim 3, wherein the halogenated alkoxy-aromatic or alkoxy-heteroaromatic compound having the general formula (II) and the catalyst are employed in a molar ratio ranging from 100:0.1 to 100:6.

5. The process according to claim 3, further comprising:
performing the process in the presence of a weak organic base selected from the group consisting of carboxylates of alkaline metals, carboxylates of alkaline-earth metals, carbonates of alkaline metals, carbonates of alkaline-earth metals, bicarbonates of alkaline metals, bicarbonates of alkaline-earth metals, and mixtures thereof.

6. The process according to claim 3, further comprising: performing the process in the presence of a weak organic base selected from the group consisting of carboxylates of alkaline metals, carboxylates of alkaline-earth metals, carbonates of alkaline metals, carbonates of alkaline-earth metals, bicarbonates of alkaline metals, bicarbonates of alkaline-earth metals and mixtures thereof, wherein the halogenated alkoxy-aromatic or alkoxy-heteroaromatic compound having the general formula (II) and the weak organic base are employed in a molar ratio ranging from 1:2.2 to 1:20.

7. The process according to claim 3, further comprising: performing the process in the presence of an organic reducing agent selected from the group consisting of hydroquinone, pyrocatechol, and para-hydroxyaminobenzene.

8. The process according to claim 3, further comprising: performing the process in the presence of an organic reducing agent selected from the group consisting of hydroquinone, pyrocatechol, and para-hydroxyaminobenzene, wherein the halogenated alkoxy-aromatic or alkoxy-heteroaromatic compound having the general formula (II) and the organic reducing agent are employed in a molar ratio ranging from 1:1.5 to 1:10.

9. The process according to claim 3, wherein the halogenated alkoxy-aromatic or alkoxy-heteroaromatic compound having the general formula (II) is employed at a molar concentration ranging from 0.1 mmoles to 10 mmoles.

10. The process according to claim 3, further comprising: performing the process in the presence of a polar aprotic organic solvent selected from the group consisting of diethyl ether ($Et_2O$), tetrahydrofuran (THF), 1,4-dioxane, dimethylsulfoxide (DMSO), N-methylpyrrolidone (NMP), N,N-dimethylformamide (DMF), and mixtures thereof.

11. The process according to claim 3, further comprising: performing the process in the presence of a polar aprotic organic solvent selected from the group consisting of diethyl ether, tetrahydrofuran, 1,4-dioxane, dimethylsulfoxide, N-methylpyrrolidone, N,N-dimethylformamide, and mixtures thereof, wherein a quantity of the halogenated alkoxy-aromatic or alkoxy-heteroaromatic compound having the general formula (II) is mixed with the dipolar aprotic organic solvent to result in a molar concentration in the solvent ranging from 0.05 mmoles to 2 mmoles.

12. The process according to claim 3, wherein the catalyst comprises a ligand selected from the group consisting of tri(t-butyl)phosphine, triphenylphosphine, tricyclohexyl-phosphonium tetrafluoroborate, 2-dicyclohexyl-phosphine-2'-(N,N-dimethyl-amino)biphenyl (DavePhos), di-t-butyl (methyl)phosphonium tetra-fluoroborate, tri-t-butyl(methyl) phosphonium tetra-fluoroborate, and mixtures thereof.

13. The process according to claim 3, further comprising: the catalyst comprising a ligand selected from the group consisting of tri(t-butyl)phosphine, triphenylphosphine, tricyclohexyl-phosphonium tetrafluoroborate, 2-dicyclohexyl-phosphine-2'-(N,N-dimethyl-amino)biphenyl, di-t-butyl(methyl)phosphonium tetra-fluoroborate, tri-t-butyl(methyl)phosphonium tetra-fluoroborate, and mixtures thereof, wherein the halogenated alkoxy-aromatic or alkoxy-heteroaromatic compound having the general formula (II) and the ligand are employed in a molar ratio ranging from 100:1 to 100:10.

14. The process according to claim 3, further comprising: performing the process at a temperature ranging from 80° C. to 170°.

15. The process according to claim 3, further comprising: performing the process for a time ranging from 12 hours to 72 hours.

16. A method comprising employing the compound according to claim 1 in constructing at least one selected from the group consisting of photovoltaic devices, solar devices, photovoltaic modules, and solar modules, on both rigid and flexible supports, wherein the compound according to claim 1 is optionally functionalized and polymerized.

17. A method comprising employing the compound according to claim 1 as a constitutive unit of luminescent solar concentrators (LSCs).

18. A method comprising employing the compound according to claim 1 as a precursor of monomeric units for preparing semiconductor polymers.

* * * * *